(12) United States Patent
Roby et al.

(10) Patent No.: US 6,764,467 B1
(45) Date of Patent: Jul. 20, 2004

(54) FIBRIN MIXTURE AND DISPENSER ASSEMBLY

(75) Inventors: Mark S. Roby, Kilingworth, CT (US); Ernie Aranyi, Easton, CT (US); Richard Yagami, Ridgefield, CT (US); H. Jonathan Tovey, Monroe, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/595,962

(22) PCT Filed: Dec. 16, 1998

(86) PCT No.: PCT/US98/26688

§ 371 (c)(1), (2), (4) Date: Jun. 19, 2000

(87) PCT Pub. No.: WO99/32155

PCT Pub. Date: Jul. 1, 1999

Related U.S. Application Data

(60) Provisional application No. 60/068,273, filed on Dec. 19, 1997.

(51) Int. Cl.[7] .................................................. A61M 5/00
(52) U.S. Cl. ........................ 604/191; 604/82; 604/416; 606/213; 606/215; 222/94; 222/129
(58) Field of Search .......................... 604/82, 191, 416; 606/213, 215; 222/134, 136, 137, 129, 145.1, 83

(56) References Cited

U.S. PATENT DOCUMENTS

| 1,948,388 | A | | 2/1934 | Liberson |
| 2,112,160 | A | | 3/1938 | Johnson |
| 2,971,793 | A | * | 2/1961 | Peterson et al. ............ 222/129 |
| 3,223,083 | A | | 12/1965 | Cobey |
| 3,236,418 | A | | 2/1966 | Dalle et al. |
| 3,467,096 | A | | 9/1969 | Horn |
| 3,521,745 | A | * | 7/1970 | Schwartzman .............. 222/129 |
| 3,521,792 | A | * | 7/1970 | Davidson .................... 222/136 |
| 3,767,085 | A | | 10/1973 | Cannon et al. |
| 3,802,604 | A | * | 4/1974 | Morane et al. ............... 222/83 |
| 4,040,420 | A | | 8/1977 | Speer |
| 4,121,739 | A | | 10/1978 | Devaney et al. |
| 4,226,235 | A | | 10/1980 | Sarnoff et al. |
| 4,260,077 | A | | 4/1981 | Schroeder |
| 4,296,786 | A | * | 10/1981 | Brignola .................... 222/83.5 |
| 4,359,049 | A | | 11/1982 | Redl et al. |
| 4,465,476 | A | * | 8/1984 | Gahwiler .................... 604/191 |
| 4,631,055 | A | | 12/1986 | Redl et al. |
| 4,673,395 | A | | 6/1987 | Phillips |
| 4,734,261 | A | | 3/1988 | Koizumi et al. |
| 4,735,616 | A | | 4/1988 | Eibl et al. |
| 4,826,048 | A | | 5/1989 | Skorka et al. |
| 4,874,368 | A | | 10/1989 | Miller et al. |

(List continued on next page.)

Primary Examiner—Thomas Denion
Assistant Examiner—Theresa Trieu

(57) ABSTRACT

A fibrin mixture and dispenser assembly is provided for mixing a first protein component with sterile water to form a first protein solution and for dispensing the first protein solution. The first protein solution forms a biological adhesive when intermixed with a second protein solution. The second protein solution is preferably mixed and dispensed by a similar fibrin mixture and dispenser assembly. The two fibrin mixture and dispenser assemblies can be housed within a single housing. The assembly includes a piercer and a first tubular extension having grooves for providing fluid communication between a reservoir and a mixing chamber or a vial. The reservoir is also in fluid communication with a dispensing needle through a second tubular extension. The reservoir is configured to contain water which is introduced to the mixing chamber. The mixing chamber is configured to contain the first protein component. The water mixes with the first protein component within the mixing chamber to form the first protein solution. The solution is transferred to the reservoir and is dispensed via the dispensing needle. The first and second components are preferably fibrinogen and thrombin which intermix either prior to or on the application site to form a fibrin sealant.

29 Claims, 11 Drawing Sheets

U.S. PATENT DOCUMENTS

| | | |
|---|---|---|
| 4,902,281 A | 2/1990 | Avoy |
| 4,978,336 A | 12/1990 | Capozzi et al. |
| 4,979,941 A * | 12/1990 | Ogle, II .................. 604/82 |
| 4,979,942 A | 12/1990 | Wolf et al. |
| 5,042,690 A * | 8/1991 | O'Meara .................. 222/83 |
| 5,116,315 A | 5/1992 | Capozzi et al. |
| 5,226,877 A | 7/1993 | Epstein |
| 5,290,259 A | 3/1994 | Fischer |
| 5,353,961 A * | 10/1994 | Debush .................. 222/129 |
| 5,368,563 A | 11/1994 | Lonneman et al. |
| 5,409,465 A | 4/1995 | Boggs et al. |
| 5,464,396 A | 11/1995 | Barta et al. |
| 5,474,540 A | 12/1995 | Miller et al. |
| 5,505,704 A | 4/1996 | Pawelka et al. |
| 5,520,658 A | 5/1996 | Holm |
| 5,582,596 A | 12/1996 | Fukunaga et al. |
| 5,643,206 A | 7/1997 | Fischer |
| 5,740,965 A | 4/1998 | Miyagi et al. |

* cited by examiner

FIBRIN MIXTURE AND DISPENSER ASSEMBLY

PRIORITY

This application claims priority to a U.S. Provisional Application filed on Dec. 19, 1997 by Roby et al. having U.S. Provisional Application Serial No. 60/068,273, the contents of which are incorporated herein by reference.

BACKGROUND

1. Technical Field

The disclosure relates generally to an assembly for mixing and dispensing one component of a tissue sealant based on human or animal proteins and, more particularly, to an assembly for forming a protein solution to be applied to tissues or organs together with another protein solution to form a fibrin sealant for sealing wounds, stopping bleeding and the like.

2. Description of Related Art

A fibrin sealant is a biological adhesive formed by mixing two protein components, namely, fibrinogen and thrombin. Each protein component is derived from human plasma and is subjected to virus elimination procedures. The components are typically individually dehydrated and stored in separate vials as sterile freeze-dried powders.

It is known that purified fibrinogen and thrombin, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until applied at the application site. These protein solutions are generally mixed and dispensed by devices such as a dual syringe apparatus.

One dual syringe apparatus for applying a fibrinogen-based tissue adhesive is disclosed in U.S. Pat. No. 4,359,049 to Redl et al. Redl et al. disclose a mechanism in which two standardized one-way syringes are held in a support having a common actuating means. The dispensing end of each syringe is inserted into a collection manifold where the two components are mixed. The components are then dispensed through a common needle capable of covering a limited area of the application site.

Typical devices for mixing and dispensing solutions of fibrinogen and thrombin require the addition of these proteins in powdered form to the body of the syringe. This makes the proteins susceptible to contamination by impurities which may enter the syringe body. Further still, the use of the syringe body to mix the proteins with water to create the protein solutions can cause the solutions to leak out from either the dispensing end of each syringe or the proximal end of the syringe body.

A dual syringe apparatus for the application of fibrinogen and thrombin solutions to an application site generally contains several parts, such as a syringe plunger, a "Y" manifold connector, a dispensing needle, a syringe holder, syringe needles, and conduits for transporting the solutions to the dispensing needle. Therefore, fibrin sealant applicators, such as disclosed in U.S. Pat. No. 4,359,049 to Redl et al. discussed above, and in U.S. Pat. No. 4,874,368 to Miller et al. and U.S. Pat. No. 4,979,942 to Wolf et al. are difficult to reuse. The replenishment of the protein components typically requires removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, adding sterile water to each syringe, replacing the syringe plunger, replacing the plunger clip, and mixing the solutions. In an application where time may be of the essence, such a lengthy replenishing process is impractical and cumbersome.

SUMMARY

A fibrin mixture and dispenser assembly is provided for mixing a first protein component with sterile water to form a first protein solution and for dispensing the first protein solution. The first protein solution forms a biological adhesive when intermixed with a second protein solution on an application site. The second protein solution is preferably mixed and dispensed by a similar fibrin mixture and dispenser assembly. The two fibrin mixture and dispenser assemblies can be housed within a single housing.

The assembly includes a piercer and a first tubular extension having grooves for providing fluid communication between a reservoir and a mixing chamber or a vial. The reservoir is also in fluid communication with a dispensing needle through a second tubular extension. The reservoir is configured to contain water which is introduced to the mixing chamber. The mixing chamber is configured to contain the first protein component. The water mixes with the first protein component within the mixing chamber to form the first protein solution. The solution is transferred to the reservoir and is dispensed via the dispensing needle. The first and second components are preferably fibrinogen and thrombin which intermix either prior to or on the application site to form a fibrin sealant.

BRIEF DESCRIPTION OF THE DRAWINGS

Various embodiments are described herein with reference to the drawings, wherein.

DETAILED DESCRIPTION OF PREFERRED EMBODIMENTS

Figure 1:
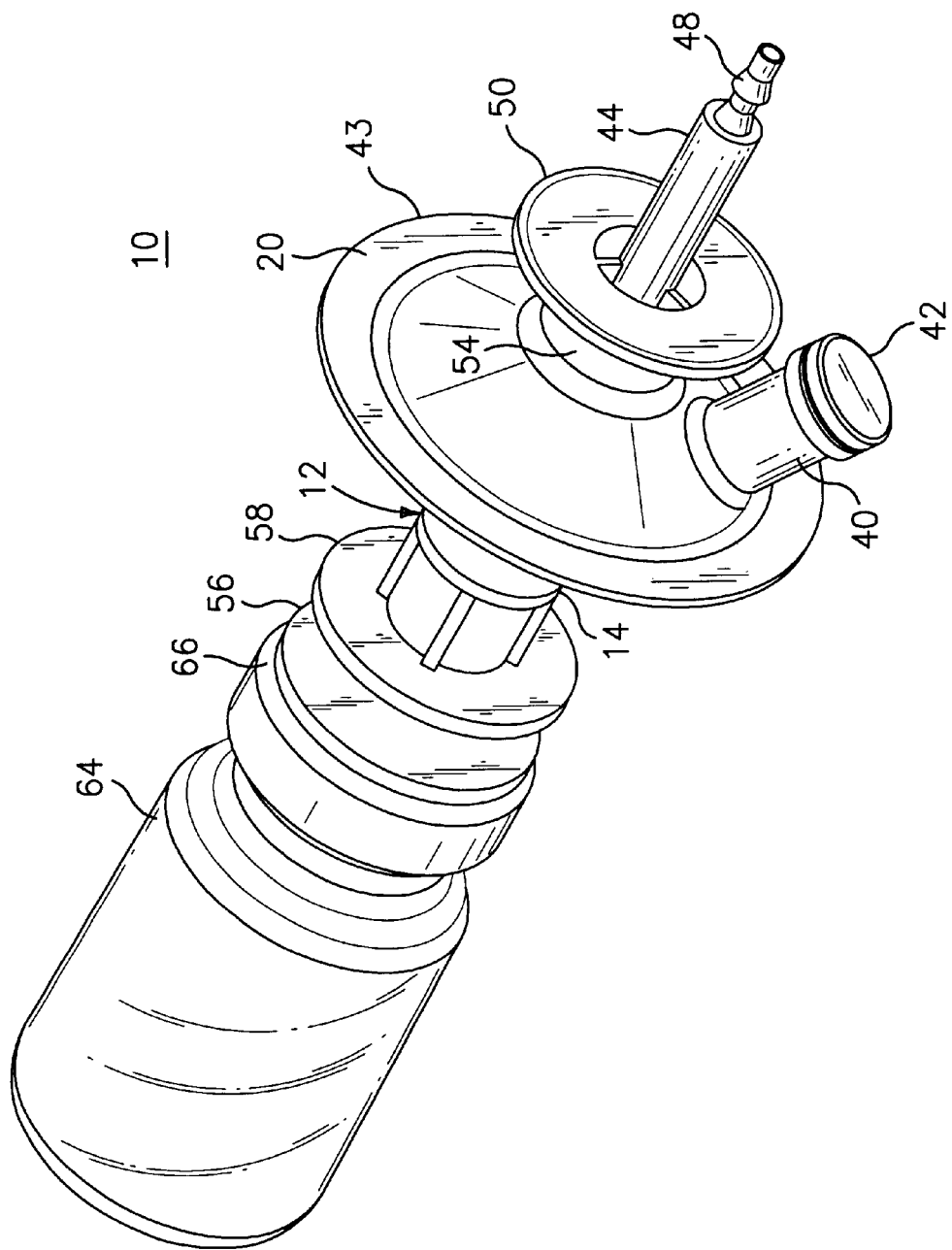
FIG. 1 is a perspective view of a preferred embodiment of a fibrin mixture and dispenser assembly.
Figure 2:
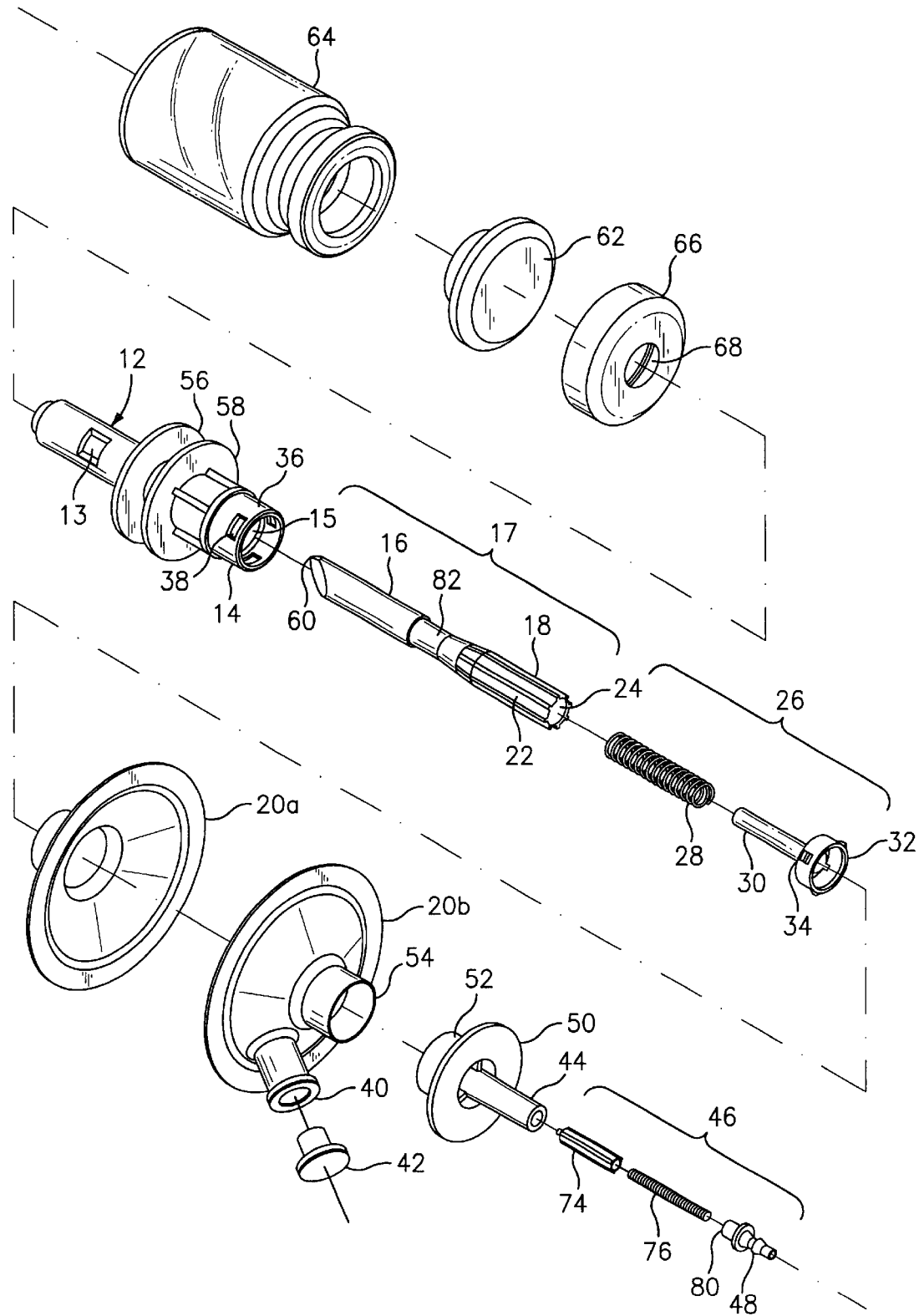
FIG. 2 is a perspective view with parts separated of the embodiment of FIG. 1 showing the assembly thereof.
Figures 3, 3A:
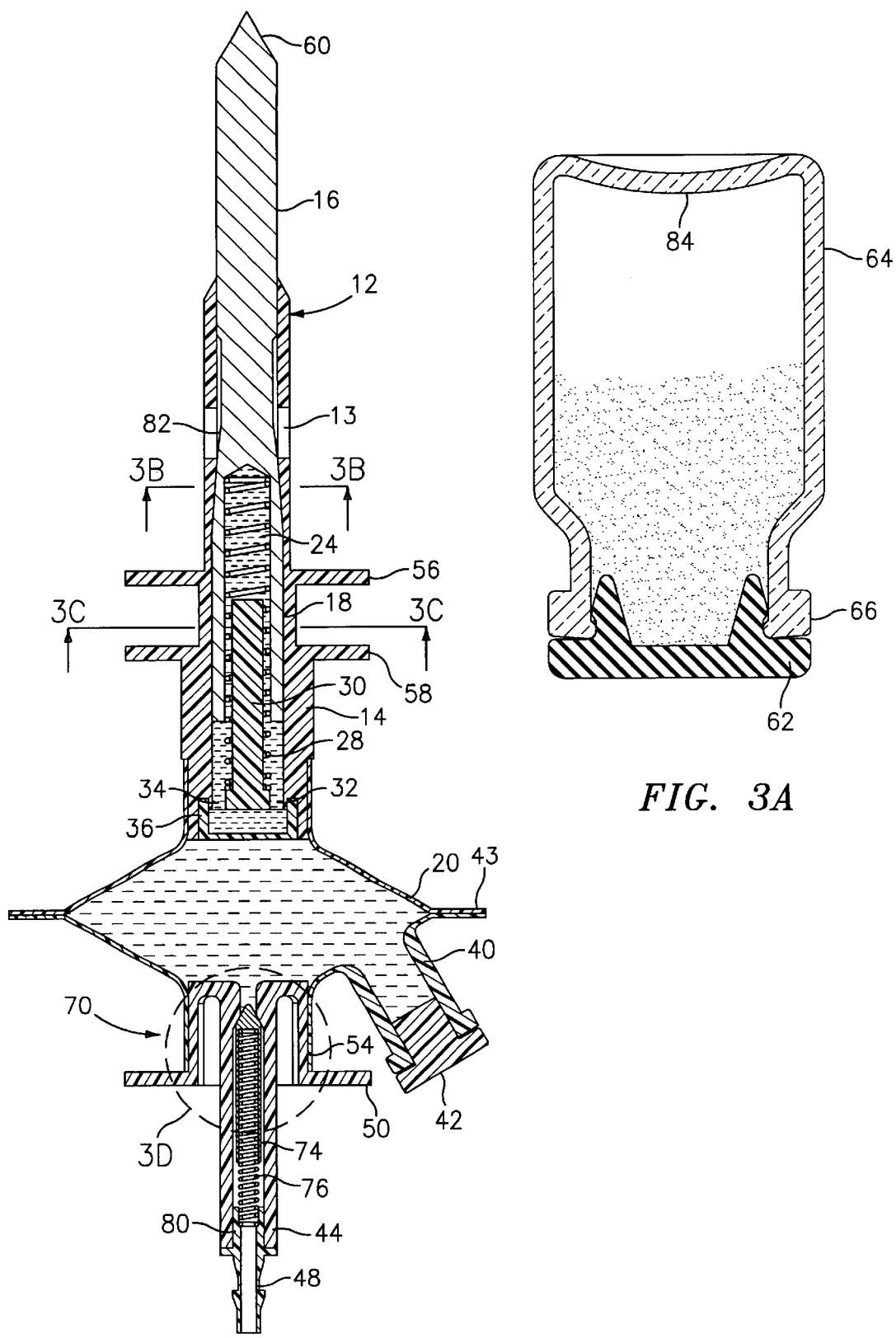
FIG. 3 is a cross-sectional view of the mixture and dispenser assembly.
FIG. 3A is an enlarged cross-sectional view of a vial having a protein component therein.
Figure 3B:
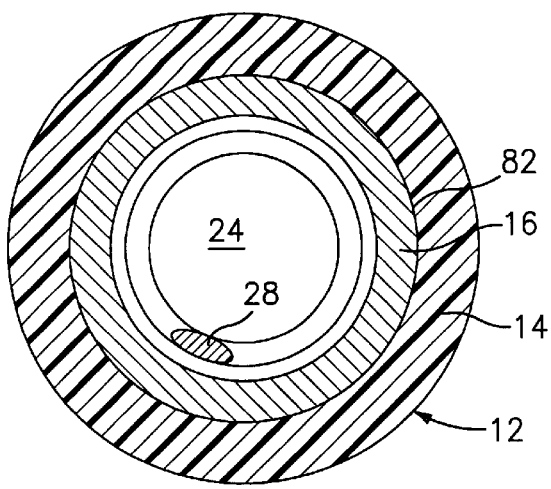
FIG. 3B is an enlarged cross-sectional view taken along line 3B—3B in FIG. 3.

Referring to FIGS. 1 and 2, a fibrin mixer and dispenser assembly according to a preferred embodiment of the present disclosure is shown. The assembly, designated generally by numeral 10, includes a longitudinal housing 12 having an elongated body portion 14 defining a longitudinal axis. A pair of flanges 56 and 58 extend perpendicular to elongated body portion 14. Elougated body portion 14 further includes apertures 13 and a bore 15 therethrough for placing a piercer 16 therein. The cross-sectional view of FIG. 3B illustrates the housing-piercer arrangement.

Figure 3C:
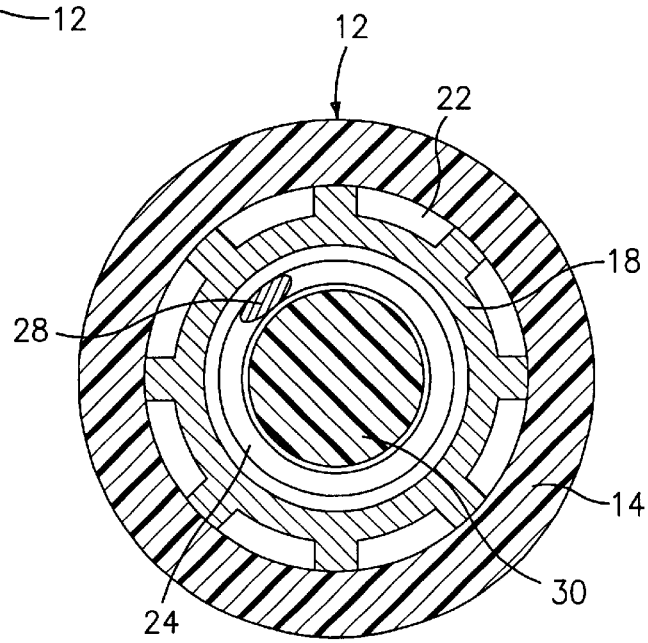
FIG. 3C is an enlarged cross-sectional view taken along line 3C—3C in FIG. 3.

The piercer 16 is connected to a first tubular extension 18 which is in fluid communication with water reservoir 20 via longitudinal grooves 22 along the surface of tubular extension 18. The longitudinal grooves 22 permit fluid to flow between the surface of tubular extension 18 and body portion 14 as illustrated by the cross-sectional view of FIG. 3C. The first tubular extension 18 further includes a bore 24 for receiving a spring-rod assembly 26. The spring-rod assembly 26 includes a spring 28 and a rod 30. A cap 32 is formed at a distal end of rod 30. The cap 32 includes apertures 34 and matingly engages cylindrical extension 36 on housing 12. Cylindrical extension 36 also includes apertures 38 which permit fluid to flow from the spring assembly 26 to and from body portion 14.

Water reservoirs 20 is in fluid communication with a second tubular extension 44 having a bore therethrough for receiving a dispensing needle assembly 46 therein. The dispensing needle assembly 46 includes a dispensing needle 48 preferably made from a metallic alloy capable of being sterilized. The second tubular extension 44 includes a circular disc 50 extending perpendicular thereto and a radially enlarged proximal end 52 for connecting the tubular extension 44 to the reservoir 20 via cylindrical extension 54 on the distal end of reservoir 20. While the water reservoir 20 is shown as being oval, it is understood that other shapes that contribute to the ease of gripping the assembly may be used.

Water reservoir 20 is in fluid communication with a second tubular extension 44 having a bore therethrough for receiving a dispensing needle 24 assembly 46 therein. The dispensing needle assembly 46 includes a dispensing needle 48 preferably made from a metallic alloy capable of being sterilized. The second tubular extension 44 includes a circular disc 50 extending perpendicular thereto and a radially enlarged proximal end 52 for connecting the tubular extension 44 to the reservoir 20 via cylindrical extension 54 on the distal end of reservoir 20. While the water reservoir 20 is shown as being oval, it is understood that other shapes that contribute to the ease of gripping the assembly may be used.

The piercer 16 is cut at an angle at a proximal end to form a pointed tip 60 for piercing a protective seal 62 on vial 64. A cap 66 having a hole 68 is placed over the protective seal 64. In this embodiment, the vial 64 contains a biological component in powdered form, preferably either thrombin or fibrinogen. The vial 64 also serves as a mixing chamber for mixing the biological component with the water in reservoir 20 as further described below. It is contemplated that the vial 64 be manufactured from a transparent plastic for a user to be able to view the amount of solution and to determine if the solution has been sufficiently intermixed. Although one embodiment for the vial 64 is illustrated and described, it is to be understood that the vial 64 could be designed in a number of different formats, including, without limitation, syringes, bags or tubing.

Figure 3D:
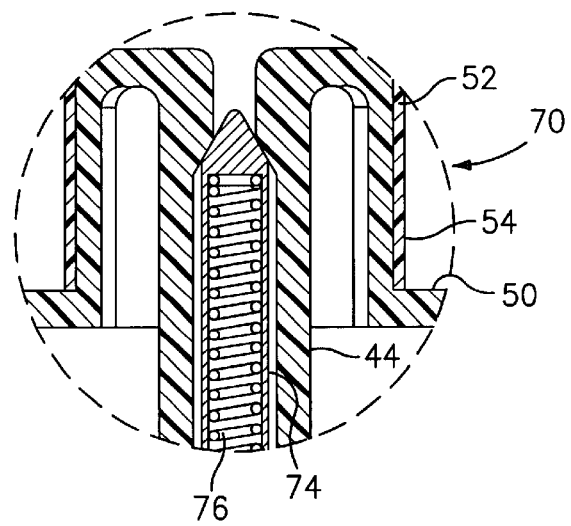
FIG. 3D is an enlarged view of a lower valve assembly shown by FIG. 3.

The assembly 10 further include a lower valve assembly 70 and an upper valve assembly 72. With reference to FIGS. 3 and 3D, lower valve assembly 70 includes the dispensing needle assembly 46 having dispensing needle 48, rod 74, and spring 76. Rod 74 includes a pointed tip 78 which is positioned within the second tubular extension 44 for preventing fluid flow as shown by the enlarged view of FIG. 3D. Spring 76 extends through rod 74. A distal end of spring 76 rests within a cylindrical extension 80 of dispensing needle 48.

Figure 4:
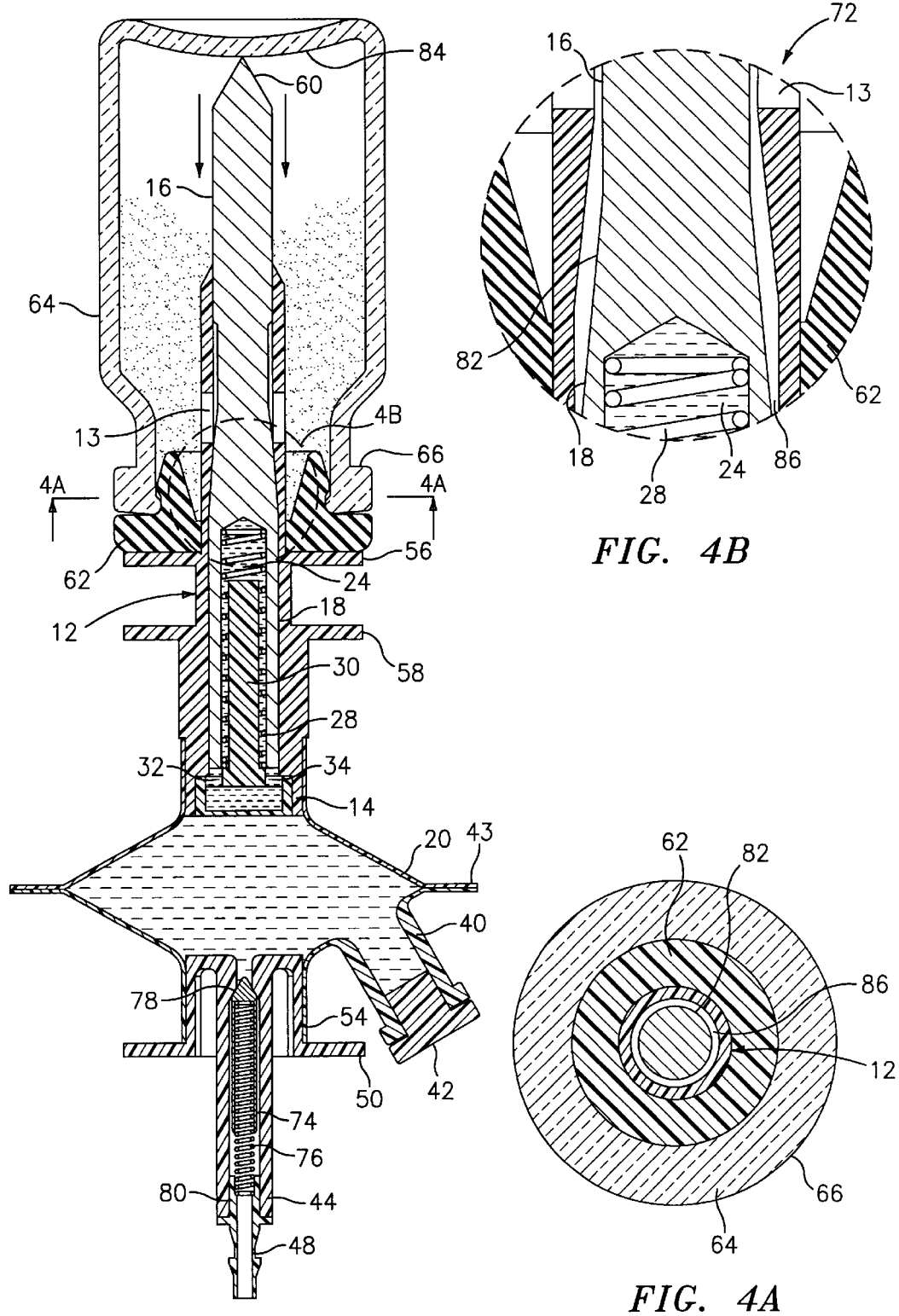
FIG. 4 is a cross-sectional view of the mixture and dispenser assembly with the vial having been secured thereto.
Figure 4B:
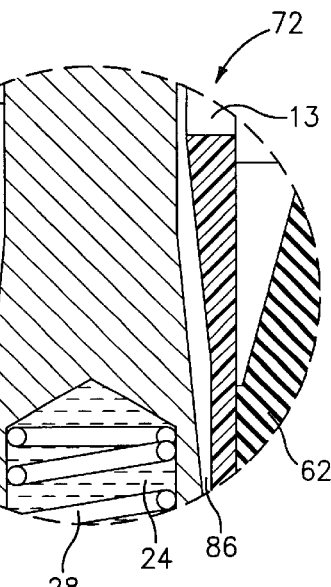
FIG. 4B is an enlarged view of an upper valve assembly.

With reference to FIGS. 4 and 4B, upper valve assembly 72 includes piercer 16 and first tubular extension 18 forming a piercer-tubular extension assembly 17.

The tubular extension 18 includes a conical proximal section 82. As shown in FIG. 4, when vial 64 is secured to assembly 20, the piercer 16 contacts a bottom surface 84 of vial 64 forcing piercer-tubular extension assembly 17 to move distally. This action causes conical section 82 to also move distally thereby creating open path 86 from which fluid can flow into and out of vial 64 depending on the gravitational orientation of assembly 10, as shown by the enlarged view of FIG. 4B.

Although the preferred embodiment has been described with a particular lower and upper valve assemblies, it is understood that other similar assemblies may be employed to achieve the same functions.

Figure 9:
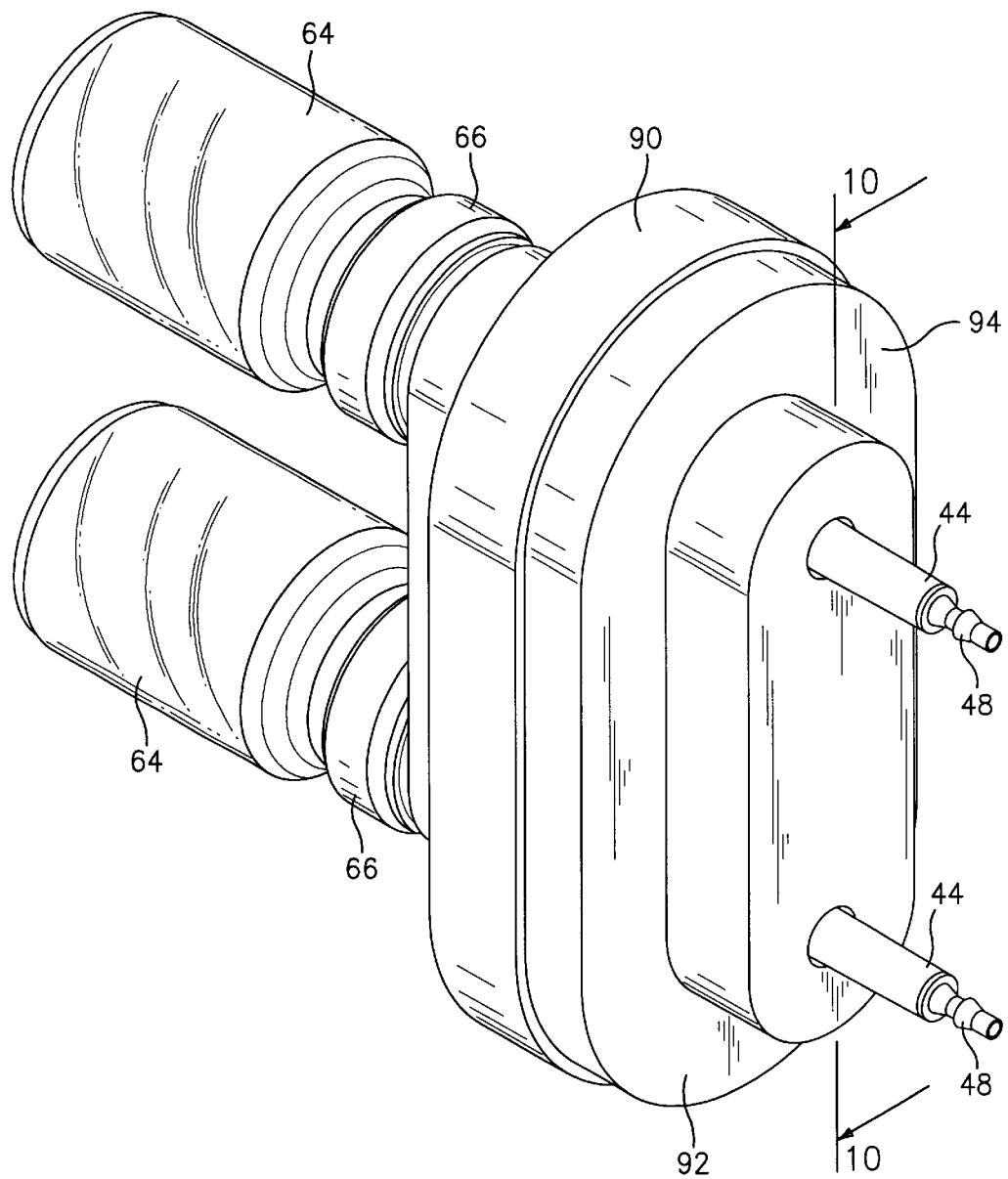
FIG. 9 is a perspective view of two fibrin mixture and dispenser assemblies housed within a single housing.

It is contemplated that two fibrin mixer and dispenser assemblies are used; one for the fibrinogen solution and another for the thrombin solution. The two fibrin mixer and dispenser assemblies can be housed within a single housing 10 as shown by FIG. 9. The two solutions can be individually dispensed via dispensing needle 48 of their respective assembly 10 directly onto an application site or to vials within a dual-dispensing applicator. The two solutions intermix on the application site to form a fibrin sealant. It is to be understood, however, that other biological fluids may be substituted, depending upon the choice of mixture that is to be dispensed. The applicator may be the type disclosed in U.S. patent application Ser. No. 08/792,535 filed on Jan. 31, 1997.

Figure 4A:
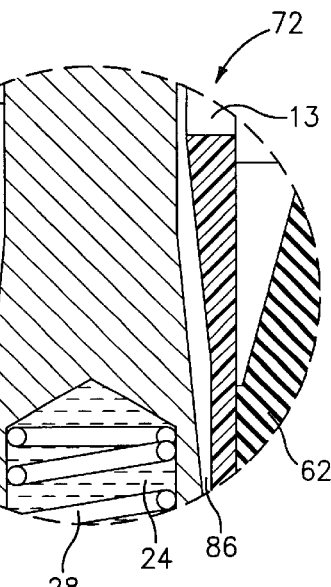
FIG. 4A is an enlarged cross-sectional view taken along line 4A–4A is FIG. 4.

The operation of assembly 10 will now be described in detail with reference to FIGS. 4–8. As discussed above with reference to FIG. 4, vial 64 is brought in proximity to piercer 16 such that protective seal 62 is pierced. This causes the piercer-extension assembly 17 to move distally as shown by the arrows in FIG. 4. As assembly 17 moves distally, conical section 82 also moves distally to form open path 86. The open path 86 is best shown in the cross-sectional view of FIG. 4A. The vial 64 is supported on assembly 10 by piercer 16 and flange 56. The assembly is positioned upright to cause the first protein component to surround apertures 13 on housing 12.

Figure 5:
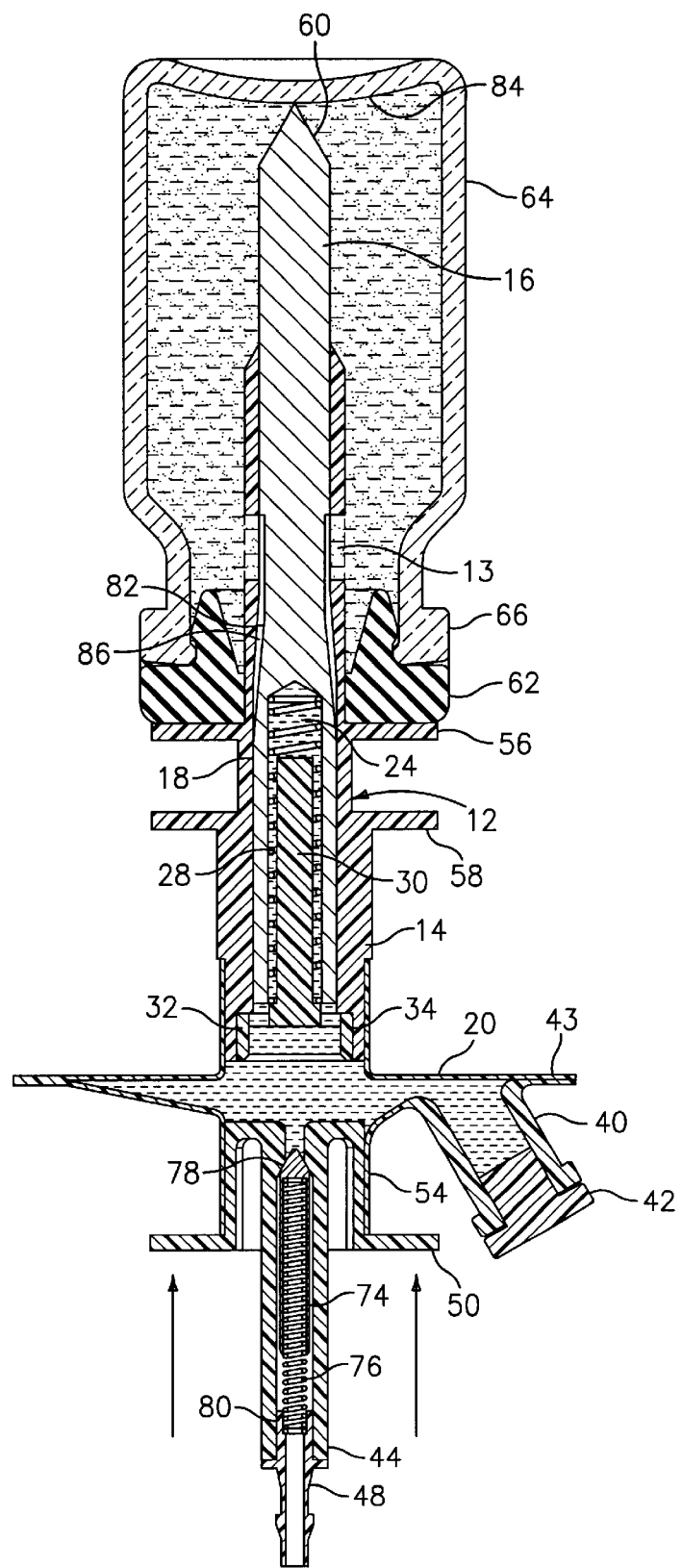
FIG. 5 is a cross-sectional view of the mixture and dispenser assembly showing the water intermixing with the protein component to form a protein solution.

Water within water reservoir 20 is introduced into vial 64 by compressing water reservoir 20 using flanges 43 and 50 as shown by FIG. 5. Compression of water reservoir 20 forces the water to flow along the grooves 22 on the surface of tubular extension 18, through path 82, through apertures 13 and into vial 64. The assembly 10 is then shaken to thoroughly intermix the protein component with the water to form a protein solution. During mixing it is preferred that the assembly 10 is turned upside-down to prevent inadequately mixed solution from flowing to the reservoir 20.

Figure 6:
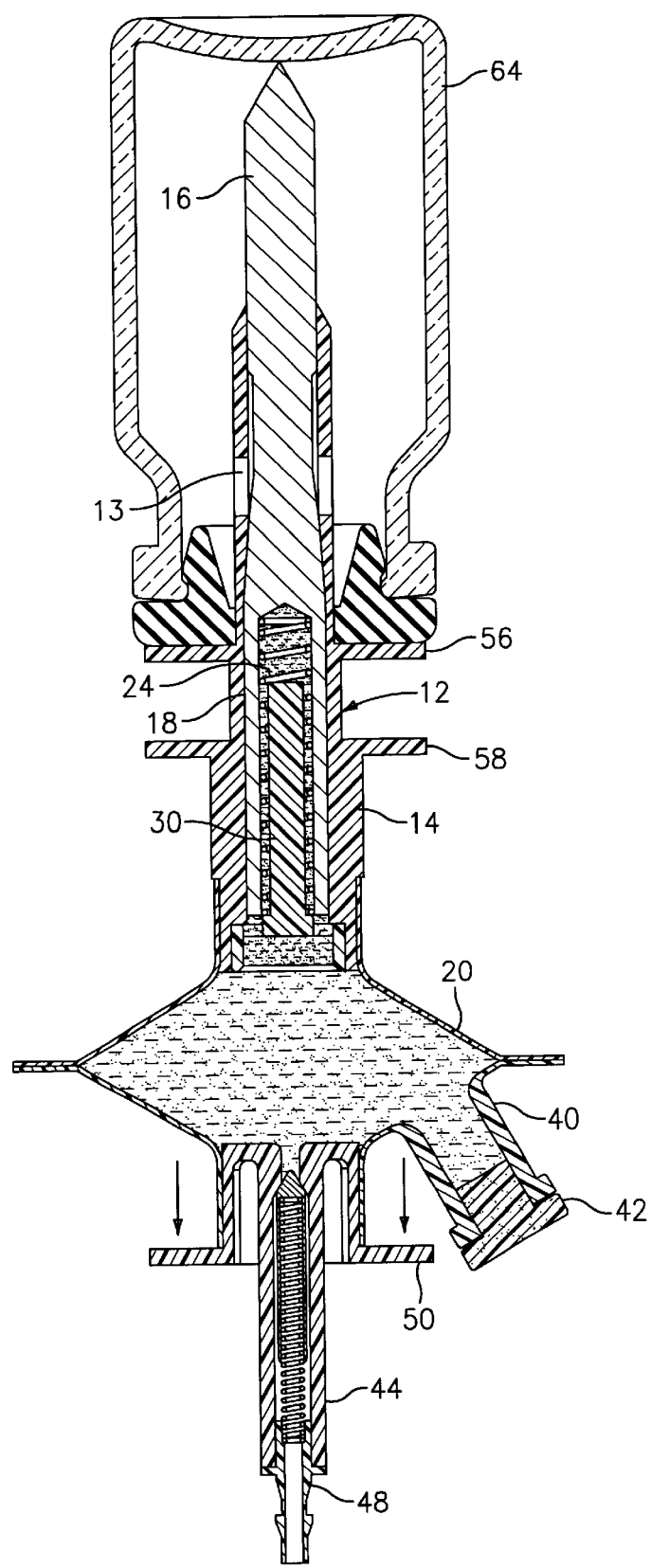
FIG. 6 is a cross-sectional view of the mixture and dispenser assembly showing the protein solution being transferred from the vial to the water reservoir.

With reference to FIG. 6, the protein solution within vial 64 is transferred to water reservoir 20 by flowing through apertures 13, through path 82, along tubular extension 18 and into water reservoir 20. When the solution has been transferred to reservoir 20, the vial 64 is removed causing the piercer-tubular extension assembly 17 to move proximally thereby also causing conical section 82 to move proximally to close off path 86 as shown by FIG. 7.

Figures 7, 8:
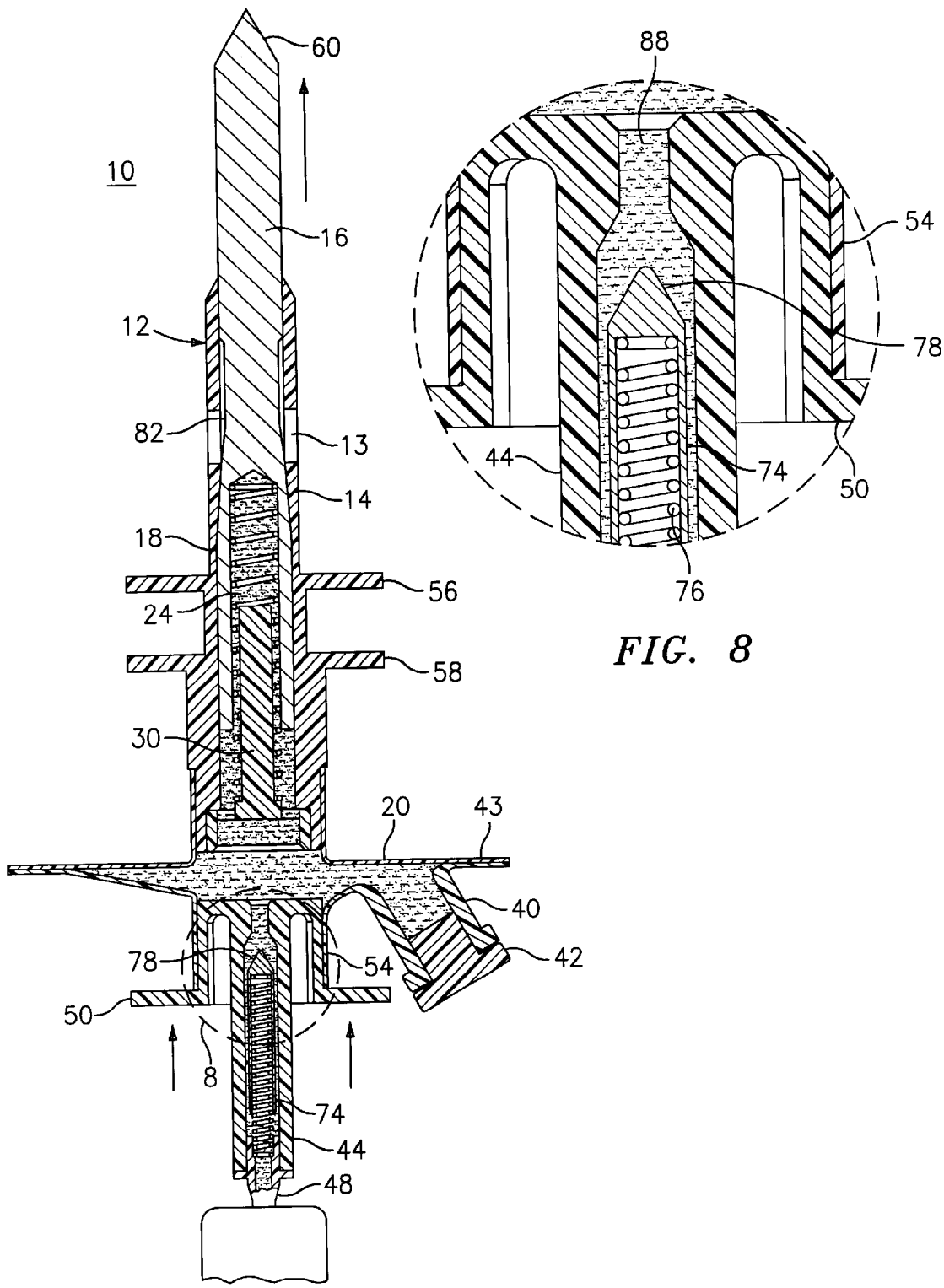
FIG. 7 is a cross-sectional view of the mixture and dispenser assembly dispensing the protein solution.
FIG. 8 is an enlarged view showing the flow of the protein solution through the lower valve assembly.

With continued reference to FIG. 7, the solution is dispensed via dispensing assembly 46 by compressing reservoir 20 by grasping flanges 43 and 50. Compression of reservoir 20 causes rod 74 to move distally creating open path 88. The solution thus flows through open path 88 as shown by the enlarged view of FIG. 8 and through dispensing needle 48.

The operation of each fibrin mixture and dispenser assembly 10 housed within housing 90 of the embodiment illustrated by FIG. 9 operates substantially the same as discussed above to form a protein solution and to dispense the same via dispensing needle 48. One of the dispenser assemblies forms the fibrinogen solution and the other forms the thrombin solution. While the housing 90 of the assembly of FIG. 9 is shown as being oval, it is understood that other shapes that contribute to the ease of operating each fibrin mixture and dispenser assembly 10 housed within housing 90 may be used.

Figure 10:
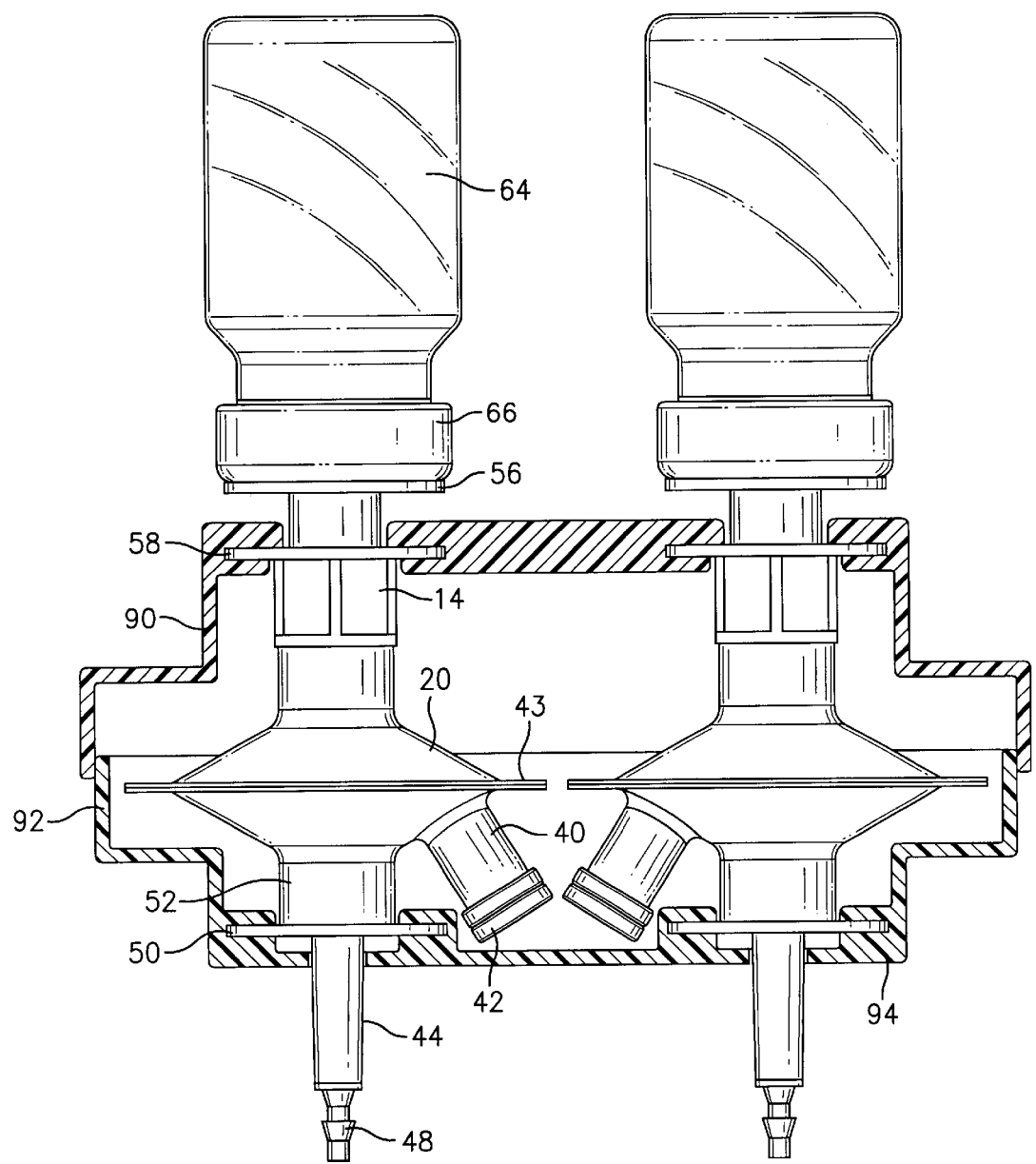
FIG. 10 is a cross-sectional view of the embodiment of FIG. 9 taken along line 10—10 in FIG. 9.
Figure 11:
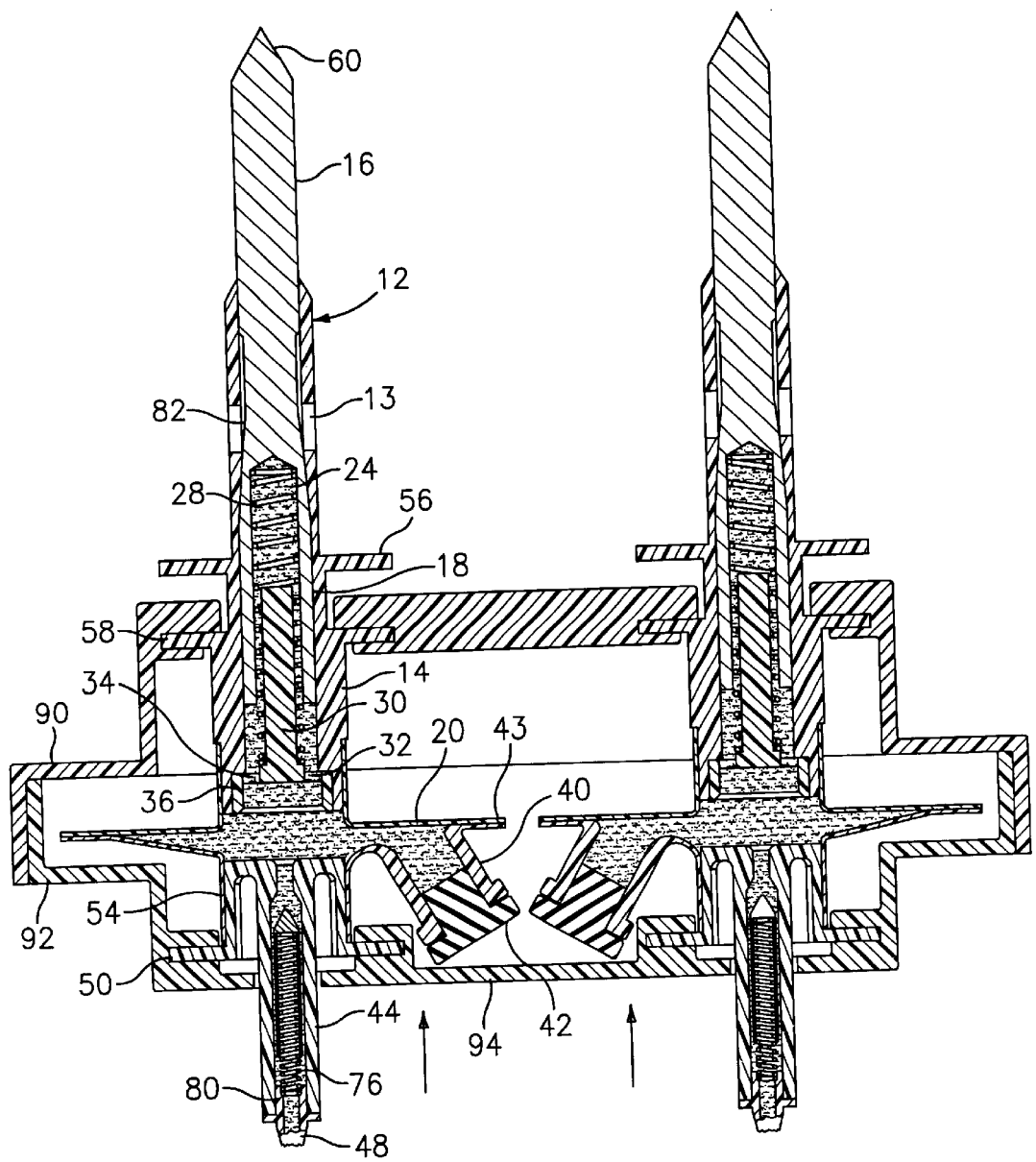
FIG. 11 is a cross-sectional view of the embodiment of FIG. 9 dispensing the protein solutions.

An activator assembly 92 is included with the housing 90 and includes a movable bottom portion 94 as shown by FIGS. 9 and 10. The movable bottom portion 94 is operatively associated with each of the reservoirs 20 to compress the reservoirs 20 to force the water therein to be transported to the vials 64 to form the protein solutions and to transport the solutions from the reservoirs 20 to each of the dispensing needles 48 as shown by FIG. 11.

It is understood that various modifications may be made to the embodiments disclosed herein to perform substantially the same function in substantially the same way to achieve substantially the same result. Also, besides applying one solution necessary to form a fibrin sealant, the fibrin mixture and dispenser assembly or each fibrin mixture and dispenser assembly within the single housing can be used to perform human or veterinary surgical procedures including applying antiseptics, medication and other similar procedures. Therefore, the above description should not be construed as limiting, but merely as exemplifications of preferred embodiments. Those skilled in the art will envision other modifications within the scope and spirit of the claims appended hereto.

What is claimed is:

1. An assembly for mixing a component of a biological adhesive with a liquid to form a solution and for dispensing the solution, the assembly comprising:
   a housing configured to receive a mixing chamber;
   a reservoir for holding a liquid, the reservoir being in fluid communication with said mixing chamber via a first path and a dispensing needle via a second path;
   a first valve assembly having a first valve moveable from a first position to a second position to open fluid communication between said reservoir and said mixing chamber via said first path when said mixing chamber is received by said housing; and
   a second valve assembly having a second valve moveable from a closed position to an open position to open fluid communication between said reservoir and said dispensing needle via said second path, wherein the volumetric capacity of said mixing chamber remains constant during mixing and dispensing of said solution.

2. The assembly of claim 1, further comprising a flange adjacent to said reservoir for aiding to open fluid communication between said reservoir and said mixing chamber and for aiding to open fluid communication between said reservoir and said dispensing needle.

3. The assembly of claim 1, further comprising a piercing needle in longitudinal alignment with said first and second paths for piercing a sealable opening of said mixing chamber.

4. The assembly of claim 1, wherein said reservoir is compressible to force contents therein through said first path and into said mixing chamber when said first valve is in said second position and to force contents within said reservoir through said second path and through said dispensing needle when said first valve is in said first position.

5. The assembly of claim 1, wherein said mixing chamber is a vial having a sealable opening capable of being pierced by a piercer longitudinally aligned with said housing.

6. The assembly of claim 3, wherein said piercing needle engages a bottom inner surface of said mixing chamber when said housing receives said mixing chamber to cause said piercing needle to move distally to move said first valve from said first position to said second position.

7. The assembly of claim 3, wherein said piercing needle is biased to move proximally when said mixing chamber is removed from said housing to move said first valve from said second position to said first position.

8. The assembly of claim 1, wherein said reservoir includes an opening for adding said liquid therein.

9. The assembly of claim 1, wherein said solution is a thrombin solution or a fibrinogen solution, whereby said biological adhesive is a fibrin sealant.

10. An assembly for mixing a component of a biological adhesive with a liquid to form a solution and for dispensing the solution, the assembly comprising:
    a housing configured to receive a first reservoir configured to contain the component;
    an activator assembly operatively associated with a second reservoir configured to contain the liquid for transporting the liquid to the first reservoir via at least one conduit in fluid communication with said first reservoir and said second reservoir for mixing with the first component to form the solution, said liquid mixes with the first component in said first reservoir to form the solution, said solution is transported from said first reservoir to said second reservoir via said at least one conduit; and
    a dispensing assembly operatively associated with said second reservoir for transporting said solution from said second reservoir through a path leading to an opening for dispensing said solution, wherein the volumetric capacity of said first reservoir remains constant during mixing and dispensing of said solution.

11. The assembly of claim 10, wherein said dispensing assembly includes a dispensing needle in fluid communication with said path for dispensing said solution as a valve of said dispensing assembly is moved from a first position to a second position.

12. The assembly of claim 10, wherein said second reservoir is compressible for forcing said liquid through said at least one conduit to transport said liquid to said reservoir.

13. The assembly of claim 10, wherein said second reservoir includes an opening for adding said liquid therein.

14. The assembly of claim 10, further comprising a flange adjacent to said second reservoir for aiding to transport the liquid to the first reservoir and for aiding to transport said solution from said second reservoir through said path.

15. The assembly of claim 10, wherein said first reservoir is a vial having a sealable opening capable of being pierced by a piercer longitudinally aligned with said housing.

16. The assembly of claim 10, wherein said activator assembly includes a valve movable from a first position to a second position for opening and closing said at least one conduit.

17. The assembly of claim 16, wherein said valve is configured to move from said first position to said second position when said first reservoir is received by said housing.

18. The assembly of claim 11, wherein said valve moves from a first position to a second position when said solution is forced through said path.

19. The assembly of claim 10, wherein said solution is a thrombin solution or a fibrinogen solution, whereby said biological adhesive is a fibrin sealant.

20. An assembly for mixing a first component of a biological adhesive with a first liquid to form a first solution, mixing a second component of the biological adhesive with a second liquid to form a second solution, and for dispensing the first and second solutions, the assembly comprising:
   a first housing configured to receive a first reservoir configured to contain the first component;
   a second housing configured to receive a second reservoir configured to contain the second component; and
   a third housing having an activator assembly operatively associated with a third reservoir configured to contain the first liquid for transporting the first liquid to the first reservoir via at least one conduit in fluid communication with said first reservoir and said third reservoir for mixing with the first component to form the first solution, said first liquid mixes with the first component in said first reservoir to form the first solution, said first solutions is transported from said first reservoir to said third reservoir via said at least one conduit, said activator assembly further operatively associated with a fourth reservoir configured to contain the second liquid for transporting the second liquid to the second reservoir via at least one conduit in fluid communication with said second reservoir and said fourth reservoir for mixing with the second component to form the second solution, said second liquid mixes with the second component in said second reservoir to form the second solution, said second solution is transported from said second reservoir to said fourth reservoir via said at least one conduit in fluid communication with said second reservoir and said fourth reservoir, said activator assembly further operatively associated with said third and fourth reservoirs for transporting said first and second solutions from said third and fourth reservoirs, respectively, through a first and a second path, respectively, leading to a first and a second opening, respectively, for dispensing said first and second solutions.

21. The assembly of claim 20, wherein said activator assembly includes a first and a second dispensing needle in fluid communication with said first and second paths, respectively, for dispensing said first and second solutions as a first and a second valve operatively associated with said first and second paths, respectively, are moved from a first position to a second position.

22. The assembly of claim 20, wherein said third and fourth reservoirs are compressible for forcing said first and second liquids therein through said at least one conduit in fluid communication with said first and third reservoirs and said at least one conduit in fluid communication with said second and fourth reservoirs to transport said first and second liquids to said first and second reservoirs, respectively.

23. The assembly of claim 20, wherein said third and fourth reservoirs include an opening for adding said first and second liquids therein.

24. The assembly of claim 20, further comprising a first flange operatively associated with said activator assembly for aiding to transport the first liquid to the first reservoir and for aiding to transport said first solution from said third reservoir through said first path, and a second flange operatively associated with said activator assembly for aiding to transport the second liquid to the second reservoir and for aiding to transport said second solution from said fourth reservoir through said second path.

25. The assembly of claim 20, wherein said first and second reservoirs are vials having a sealable opening capable of being pierced by a first and a second piercer, respectively, longitudinally aligned with said first and second housing.

26. The assembly of claim 20, further comprising a first valve movable from a first position to a second position for opening and closing said at least one conduit in fluid communication with said first and third reservoirs, and a second valve movable from a first position to a second position for opening and closing said at least one conduit in fluid communication with said second and fourth reservoirs.

27. The assembly of claim 26, wherein said first valve is configured to move from said first position to said second position when said first reservoir is received by said first housing and said second valve is configured to move from said first position to said second position when said second reservoir is received by said second housing.

28. The assembly of claim 21, wherein said first and second valve move from a first position to a second position when said first and second solutions are forced through said first and second paths, respectively.

29. The assembly of claim 20, wherein said first solution is a thrombin solution and said second solution is a fibrinogen solution, whereby said biological adhesive is a fibrin sealant.

* * * * *